United States Patent [19]
Chavkin et al.

[11] Patent Number: 4,980,175
[45] Date of Patent: Dec. 25, 1990

[54] LIQUID ORALLY ADMINISTRABLE COMPOSITIONS BASED ON EDIBLE OILS

[76] Inventors: Leonard Chavkin, R.R. 1 Box 90, Bloomsbury, N.J. 08804; Leonard Mackles, 311 E. 23rd St., New York, N.Y. 10010

[21] Appl. No.: 293,194

[22] Filed: Jan. 3, 1989

[51] Int. Cl.$^5$ .................. A01N 59/08; A01N 59/06; A01N 43/04; A01N 37/00

[52] U.S. Cl. .................. 424/677; 424/682; 424/686; 424/687; 424/690; 424/692; 424/693; 514/53; 514/54; 514/574; 514/937

[58] Field of Search ............... 514/557, 786, 925, 937, 514/53, 54, 574, 937, 715, 717; 424/489, 498, 677, 682, 686, 687, 690, 692, 693

[56] References Cited

U.S. PATENT DOCUMENTS

| | | |
|---|---|---|
| 2,988,483 | 6/1961 | Barsky et al. .................. 167/82 |
| 3,244,834 | 4/1966 | Buddemeyer et al. .................. 99/91 |
| 4,294,819 | 10/1981 | Tencza .................. 424/14 |
| 4,339,428 | 7/1982 | Tencza .................. 424/21 |
| 4,639,367 | 1/1987 | Mackles .................. 424/45 |
| 4,664,915 | 5/1987 | Simonian .................. 424/128 |
| 4,752,465 | 6/1988 | Mackles .................. 424/45 |
| 4,786,495 | 11/1988 | Bird et al. .................. 424/81 |
| 4,797,288 | 1/1989 | Sharma et al. .................. 424/476 |
| 4,889,709 | 12/1989 | Mackles et al. .................. 424/45 |

*Primary Examiner*—Douglas W. Robinson
*Assistant Examiner*—T. Criares
*Attorney, Agent, or Firm*—Omri M. Behr

[57] ABSTRACT

Orally ingestible liquid compositions for suspending therein orally administrable pharmaceutically active compositions comprising triglycerides, propylene glycol ester, or monoacetylated glycerides of medium chain length alkanoic acids, polyglycerol esters, and colloidal silicon dioxide.

14 Claims, No Drawings

LIQUID ORALLY ADMINISTRABLE COMPOSITIONS BASED ON EDIBLE OILS

FIELD OF THE INVENTION

Liquid carriers for administration of large doses of pharmaceutically active compositions.

BACKGROUND OF THE INVENTION

A very large number of pharmaceutically active materials may be administered in exceedingly small doses and may thus, when orally administrable, be taken in the form of tablets or capsules. Other materials may be compounded in liquid form in solutions, elixirs or the like. There is however, another class of pharmaceutically active materials which require the administration of rather substantial quantities in order to achieve the desired end. Most of these materials are utilized for the treatment of gastric disturbances. Included in this group are gums used as gastric ulcer-relief agents, mucosal bio-adhesives, anti-gastric ulcer agents, and, as the largest group, inorganic gastric acid neutralizing agents commonly known as antacids. These materials which exist as powders or gums, present special problems of preparation in administrable form. In the case of antacids, it has long been considered desirable to administer a dose not exceeding 10 ml. which contain sufficient antacid to have an acid neutralizing capacity (ANC) of 80 mEq. or more.

While aqueous suspensions of antacids have been known for decades, it has not been possible heretofore to reach the desired level of neutralizing capacity. The reason is that the amount of antacid required is about 3 grams and cannot be physically suspended in the usual aqueous vehicles employed for this purpose, since the products thus produced are too thick, do not flow, cake and/or are impossible to redisperse. Furthermore, even where such a product can be made, the taste is so objectionable that no patient could be persuaded to use it. A further disadvantage of aqueous systems is that they can act as hosts to microbial growth which, in turn, requires the use of bad tasting preservatives such as parabens and benzoates. Thus, the provision of a non-aqueous liquid suspension system would be desirable.

It would be clear to one skilled in the art that low viscosity edible oils would be a desirable principal vehicle for such suspensions. Unfortunately, closer examination reveals that many low viscosity edible oils are not suitable for this purpose. Mineral oils cannot be used as vehicles for liquid antacid products, since they are not digestible and tend to leak from the consumer's anus.

Low viscosity vegetable oils such as corn, cotton seed, safflower, soybean and rapeseed oils, initially appear to be viable carriers but, in fact are not suitable, because of their relatively long hydrocarbon chain, i.e., 12 to 18 carbon atoms, which leads to an undesirably high level of viscosity. This viscosity can be lowered if unsaturation is present and a significant amount of linoleic or linolenic triglycerides are present. However, the introduction of unsaturation introduces the problem of rancidification, which in turn, precludes satisfactory long-term product stability.

In order to make an oil based product consumer acceptable, it is necessary to eliminate the oily taste by the incorporation of an edible surfactant. The widely used ethoxylated sorbitan esters (Tweens) and other ethoxylated or propoxylated ester surfactants have their own taste problems and therefore, cannot be utilized at levels exceeding about 1% of the finished product. This level would be insufficient to solve the problems of the projected composition of the present invention.

Finally, it is desirable to utilize a suspending agent to prevent aggregation and cake formation in the suspensions. Suspending agents in general are well known. However, it has been found that the more common suspending agents such as for example, clays such as bentonite, attapulgite or magnesium aluminum silicate, do not function well in the presence of high loadings of antacids in an oil medium. The formulation therefore of a suspending medium having a satisfactory, low viscosity oil as its base and associated with it, taste suppressing agents and suspending agents, all of which are compatible with a high loading of pharmaceutically active material, is a substantial problem which has required a considerable amount of work in its solution.

The normally used antacid actives as recognized in the official FDA final monograph on antacids as part of their OTC Drug review published in 1981. These include basic aluminum salts, particularly aluminum hydroxide, dried gel USP; basic magnesium salts, i.e., magnesium trisilicate USP, magnesium hydroxide USP, magnesium oxide USP and magnesium carbonate USP; basic calcium salts, particularly calcium carbonate USP, basic sodium or potassium salts, particularly sodium or potassium bicarbonate. The acceptable forms of these ingredients are fine, dense powders.

Alginic acid and other gums such as carrageenan, polycarbophil and anti-ulcer actives such as sucralfate can also be used.

Carrageenan has been suggested to have an anti-ulcer effect and sucralfate is widely used for the same reason. Both act directly on the site of the exposed ulcer and have the ability to spread a fine film over the gastric mucosa. High doses are required for optimum efficacy of these agents.

Alginic acid has been widely used in antacid products. It is especially useful for the treatment of esophageal reflux, a condition in which acid gastric contents are regurgitated upward into the esophagus causing significant pain and irritation of the lower esophagus. The consumer describes this condition as "heartburn". It is a frequent complication experienced by sufferers with hiatal hernias. Alginic acid works against this reflux by reacting with a basic ingredient in the system, e.g., sodium bicarbonate or magnesium hydroxide to form a soluble alginate that forms a gel in the water in the stomach. The carbon dioxide released by this reaction and by the reaction of carbonates in the formula with the hydrochloric acid present in the stomach is trapped in the alginate gel as bubbles and cause the gel to float on the stomach contents. This gel coats the gastro-esophageal area at the cardiac sphincter of the stomach and prevents the gastric acid of the stomach from refluxing into the esophagus.

Polycarbophil and the alginates have been described as bio-adhesive agents. This means that they tend to stick to moist mucosal surfaces and have been shown to hold medication at that site for slow release. When such ingredients are incorporated in the present suspensions, the result is a much longer residence time in the stomach which makes for a much longer duration of antacid action. Normal doses of conventional antacid products last in the stomach only for about 45 minutes. With this "bio-adhesive" system (antacid and gum) and the large amount of antacid delivered, duration of 6–8 hours can be expected and for the first time, an antacid product is available that can help the sufferer of hyperacidity sleep through the night.

In addition, calcium polycarbophil USP is a recognized therapeutic agent for the gastrointestinal tract. In fact, the FDA permits its sale directly to the consumer, both as a laxative and an antidiarrheal agent. It acts by absorbing water, forming a gel and promoting well-formed stools. The dose however is up to 6 grams per day for adults and 3 grams per day for children 6–12 years of age. It is marketed solely as chewable tablets of 0.5 grams, which are gritty and unpleasant to take. It is impossible to market an aqueous suspension, since by its nature, it would cause aqueous systems to gel.

Using the present invention it is possible to prepare fluid suspensions containing 20% of calcium polycarbophil. This suspension is very palatable and permits the easy administration of the large doses of polycarbophil necessary for optimum therapeutic efficacy.

SUMMARY OF THE INVENTION

There is provided an orally ingestible liquid composition for suspending therein at least one orally administrable pharmaceutically active composition comprising at least one triglyceride, propylene glycol ester or acetylated monoglyceride of a medium chain length alkanoic acid, at least one liquid, high HLB polyglycerol ester, and colloidal silicon dioxide.

The actual administrable composition further comprises at least one pharmaceutically active composition.

DESCRIPTION OF THE PREFERRED EMBODIMENTS

There is provided an orally ingestible liquid composition for suspending therein at least one orally administrable pharmaceutically active composition comprising an oil, suitably about 40 to about 70 parts by weight of at least one triglyceride or propylene glycol ester of a medium chain length alkanoic acid wherein the said acid has between 8 and 10 carbon atoms in the chain or at least one acetylated monoglyceride of at least one medium chain length alkanoic acid, having hydroxyl value of 0–15, an acetylation level of at least 95% and a melting point between about 4° and about 12° C., about 2 to about 15 parts by weight of a liquid, high HLB polyglycerol ester, and about 1 to about 5 parts by weight of colloidal silicon dioxide to a total of between about 50 and about 90 parts by weight.

The actual administrable composition further comprises about 10 to about 50 parts by weight, to a total composition of 100 parts by weight of at least one pharmaceutically active composition.

Preferably, the alkanoic acid of the preferred oil is caprylic or capric acid, the ester is liquid at least 20° C. and the HLB is at least 8.0. The polyglycerol ester is suitably at least one member of the group consisting of hexaglycerol monooleate, octaglycerol monooleate and hexaglycerol dioleate.

Commercially available examples of the foregoing oils are medium chain triglycerides such as Neobee O and Neobee M5, manufactured by PVO International; Miglycol 810, 812, 818, 829 and 840, manufactured by Dynamit Nobel; Captex 200, 300, 350, 355 and 810B, manufactured by Capitol City Products and acelylated monoglycerides such as Myvacet 9-45K, manufactured by Eastman Kodak.

It is desirable that silicon dioxide is hydrophilic fumed silicon dioxide.

In addition to the essential ingredients described above, the products can contain other ingredients included for special purposes. These include flavors, colors, natural and artificial sweeteners, preservatives, silicone antiflatulent actives (i.e., Simethicone) and others.

As the pharmaceutically active agent there may be utilized at least one member of the group consisting of inorganic gastric acid neutralizing agents, gums used as gastric ulcer relief agents, mucosal bioadhesives and anti gastric ulcer agents.

Suitably, as neutralizing agents there may be utilized a basic salt of aluminum, magnesium, bismuth and calcium or a hydroxide suboxide or carbonate thereof. As gums there may be used carrageenan, alginic acid and the pharmaceutically acceptable alkali metal salts thereof. There may also be employed bioadhesives such as polycarbophil and anti-ulcer agents such as sucralfate.

It will be understood by those skilled in the art that the suspending composition may be employed in conjunction with any orally administrable pharmaceutically active agents. It is particularly useful however with those agents, especially those in powdered form, which must be administered in relatively large amounts.

EXAMPLE 1

| FORMULA | % (W/W) |
| --- | --- |
| 1. Aluminum hydroxide, USP dried gel | 10.0 |
| 2. Magnesium hydroxide, USP heavy powder | 10.0 |
| 3. Calcium carbonate, USP | 10.0 |
| 4. Colloidal silicon dioxide, N.F. | 2.0 |
| 5. Medium chain triglycerides | 47.5 |
| 6. Hexaglycerol monooleate | 10.0 |
| 7. Sugar 12X, N.F. | 10.0 |
| 8. Lemon mint flavor | 0.5 |
| | 100.0% |

PROCESS

A. Mix 5 and 6 and heat to 60° C.
B. Add 2, 3, 4 and 7 and disperse with vigorous mixing.
C. Cool to below 40° C. and add 8+1*. Continue mixing until uniform dispersion is obtained.

*The aluminum hydroxide is added to the product when cool, since it begins to decompose and lose its acid neutralizing power when exposed to high temperatures.

D. Pass through homogenizer or colloid mill to disperse any aggregates.

In accordance with the above procedure but where in place of hexaglycerol monooleate, there is utilized hexaglycerol dioleate, a similar composition is obtained.

In accordance with the above procedure but where in place of aluminum hydroxide, there is utilized bismuth subcarbonate a similar composition is obtained.

In accordance with the above procedure but where in place of the medium chain triglycerides the corresponding propylene glycol esters are used, a similar composition is obtained.

EXAMPLE 2

| FORMULA | % (W/W) |
| --- | --- |
| 1. Aluminum hydroxide, USP dried gel | 15.0 |
| 2. Magnesium hydroxide, USP heavy powder | 15.0 |
| 3. Colloidal silicon dioxide, NF | 2.0 |
| 4. Medium chain triglycerides | 47.5 |
| 5. Hexaglycerol monooleate | 10.0 |
| 6. Sugar, 12X, NF | 10.0 |

-continued

| FORMULA | % (W/W) |
|---|---|
| 7. Lemon mint flavor | 0.5 |
| | 100.0% |

PROCESS

A. Mix 4 and 5 and heat to 60° C.
B. Add 2, 3 and 6 and disperse with vigorous mixing.
C. Cool to below 40° C. and add 1 and 7. Continue mixing until uniform dispersion is obtained.
D. Pass through homogenizer or colloid mill to disperse any aggregates.

In accordance with the above procedure but where in place of hexaglycerol monooleate, there is utilized octaglycerol monooleate, a similar composition is obtained.

In accordance with the above procedure but where in place of the medium chain triglycerides the corresponding propylene glycol esters are used, a similar composition is obtained.

EXAMPLE 3

| FORMULA | % (W/W) |
|---|---|
| 1. Aluminum hydroxide, dried gel USP | 7.0 |
| 2. Magnesium hydroxide, USP | 7.0 |
| 3. Magnesium carbonate, USP | 7.0 |
| 4. Calcium carbonate, USP | 10.0 |
| 5. Alginic acid, powder | 5.0 |
| 6. Hexaglycerol monooleate | 5.0 |
| 7. Sugar 12X, NF | 10.0 |
| 8. Medium Chain Triglycerides | 48.5 |
| 9. Lemon Mint Flavor | 0.5 |
| | 100.0% |

PROCESS

A. Mix 6 and 8 and heat to 60° C.
B. Add 2, 3, 4, 5 and 7 and disperse with vigorous agitation.
C. Cool to below 40° C. and add 1 and 9. Mix until uniform.
D. Pass through homogenizer or colloid mill to disperse any aggregate.

EXAMPLE 4

Sucralfate Suspension

Each teaspoonful (5 ml.) contains 1 grams of Sucralfate.

| Formula | % (W/W) |
|---|---|
| 1. Sucralfate (fine powder) | 20.0 |
| 2. Sugar, 12X | 20.0 |
| 3. Cab-O-Sil M-5 | 20.0 |
| 4. Hexaglycerol monooleate | 8.0 |
| 5. Saccharin, insoluble | 0.1 |
| 6. Lemon mint flavor | 0.3 |
| 7. Medium chain triglycerides | 49.6 |
| | 100.0% |

PROCESS

A. Mix 4 and 7 and heat to 60° C.
B. Add 1, 2, 3, and 5 and disperse with vigorous mixing.
C. Cool to below 40° C. and add 6. Continue mixing until uniform dispersion is obtained.
D. Pass through homogenizer or colloid mill to disperse any aggregates.

EXAMPLE 5

Polycarbophil Suspension

Each teaspoonful (5 ml.) contains 1.0 gram of calcium polycarbophil.

| Formula | % (W/W) |
|---|---|
| 1. Carbophil C-977 (calcium polycarbophil USP) | 20.0 |
| 2. Sugar, 12X | 20.0 |
| 3. Cab-O-Sil M-5 | 2.0 |
| 4. Hexaglycerol monooleate | 8.0 |
| 5. Saccharin, insoluble | 0.1 |
| 6. Lemon mint flavor | 0.3 |
| 7. Medium chain triglycerides | 49.6 |
| | 100.0% |

In accordance with the above procedure but where in place of the medium chain triglycerides the corresponding propylene glycol esters are used, a similar composition is obtained.

PROCESS

A. Mix 5 and 6 and heat to 60° C.
B. Add 2, 3, 4 and 7 and disperse with vigorous mixing.
C. Cool to below 40° C. and add 6+1. Continue mixing until uniform dispersion is obtained.
D. Pass through homogenizer or colloid mill to disperse any aggregates.

We claim:

1. An orally ingestible liquid composition for suspending therein at least one orally administrable pharmaceutically active agent, said composition comprising:
    (a) about 40 to about 70 parts by weight of a member of the group consisting of at least one triglyceride or propylene glycol ester of a medium chain length alkanoic acid, wherein at least 95% by weight of the said acid has between 8 and 10 carbon atoms in the chain and at least one acetylated monoglyceride of at least one medium chain length alkanoic acid, having hydroxyl value of 0-15, an acetylation level of at least 95% and a melting point between about 4° and about 12° C.,
    (b) about 2 to about 15 parts by weight of a polyglycerol ester, liquid at least 20° C. and having an HLB of at least 8.0,
    (c) about 1 to about 5 parts by weight of colloidal silicon dioxide to a total of between about 50 and about 90 parts by weight.

2. A composition of claim 1 wherein the alkanoic acid of (a) is caprylic or capric acid.

3. A composition of claim 1 wherein the polyglycerol ester is selected from at least one member of the group consisting of hexaglycerol monooleate, octaglycerol monooleate and hexaglycerol dioleate.

4. A composition of claim 1 wherein the silicon dioxide is hydrophilic fumed silicon dioxide.

5. An orally ingestible liquid composition having suspended therein at least one orally administrable pharmaceutically active agent, said composition comprising:
    (a) about 40 to about 70 parts by weight of at least one triglyceride or propylene glycol ester of a medium chain length alkanoic acid wherein the said acid has between 8 and 10 carbon atoms in the chain and at least one acetylated monoglyceride of at least one medium chain length alkanoic acid having hydroxyl value of 0-15, an acetylation level of at least 95% and a melting point between about 4° and about 12° C.,
(b) about 2 to about 15 parts by weight of a polyglycerol ester, liquid at least 20° C. and having an HLB of at least 8.0,
(c) about 1 to about 5 parts by weight of colloidal silicon dioxide and
(d) about 10 to about 50 parts by weight, to a total composition of 100 parts by weight, of said at least one pharmaceutically active composition.

6. A composition of claim 5 wherein the alkanoic acid of (a) is caprylic or capric acid.

7. A composition of claim 5 wherein the polyglycerol ester is liquid at least 20° C. and the HLB is at least 8.0.

8. A composition of claim 7 wherein the polyglycerol ester is selected from at least one member of the group consisting of hexaglycerol monooleate, octaglycerol monooleate and hexaglycerol dioleate.

9. A composition of claim 5 wherein the silicon dioxide is hydrophilic fumed silicon dioxide.

10. A composition of claim 5 wherein at least one pharmaceutically active agent is selected from the group consisting of inorganic gastric acid neutralizing agents, gums used as gastric ulcer relief agents, mucosal bioadhesives and anti-gastric ulcer agents.

11. A composition of claim 10 wherein at least one pharmaceutically active agent is selected from the group consisting of a basic salt of aluminum, magnesium, bismuth and calcium or a hydroxide or carbonate thereof.

12. A composition of claim 10 wherein at least one pharmaceutically active agent is selected from the group consisting of a carbonate or bicarbonate of sodium or potassium.

13. A composition of claim 10 wherein at least one pharmaceutically active agent is selected from the group consisting of carrageenan, alginic acid and the pharmaceutically acceptable alkali metal salts thereof.

14. A composition of claim 10 wherein at least one pharmaceutically active agent is selected from the group consisting of polycarbophil and sucralfate.

* * * * *

UNITED STATES PATENT AND TRADEMARK OFFICE
CERTIFICATE OF CORRECTION

PATENT NO. : 4,980,175

DATED : 12/25/90

INVENTOR(S) : Chavkin, et al.

It is certified that error appears in the above-identified patent and that said Letters Patent is hereby corrected as shown below:

Column 5, Example 3, line 34 after item number 9 insert as a new line --10. Cab-O-Sil M5  2.0--.
line 33, delete "48.5" insert --46.6--.
Column 5, line 56, in item number 3 delete "20.0" insert --2.0--.

Signed and Sealed this

Twenty-third Day of June, 1992

Attest:

DOUGLAS B. COMER

Attesting Officer

Acting Commissioner of Patents and Trademarks